(12) United States Patent
Huang et al.

(10) Patent No.: US 7,283,220 B2
(45) Date of Patent: Oct. 16, 2007

(54) METHODS AND APPARATUSES FOR MEASURING THE REFRACTIVE INDEX AND OTHER OPTICAL PROPERTIES OF LIQUIDS, GELS, AND SOLIDS

(75) Inventors: Lidu Huang, Danville, CA (US); Alexei Glebov, San Mateo, CA (US); Shigenori Aoki, Sunnyvale, CA (US); Michael G. Lee, San Jose, CA (US); Kishio Yokouchi, San Jose, CA (US)

(73) Assignee: Fujitsu Limited, Kanagawa (JP)

( * ) Notice: Subject to any disclaimer, the term of this patent is extended or adjusted under 35 U.S.C. 154(b) by 424 days.

(21) Appl. No.: 10/808,665

(22) Filed: Mar. 24, 2004

(65) Prior Publication Data

US 2005/0213080 A1 Sep. 29, 2005

(51) Int. Cl.
*G01N 21/41* (2006.01)

(52) U.S. Cl. ...................................... 356/128

(58) Field of Classification Search ................. 356/128
See application file for complete search history.

(56) References Cited

U.S. PATENT DOCUMENTS

| | | | | |
|---|---|---|---|---|
| 3,950,104 A | * | 4/1976 | Munk | 356/128 |
| 4,213,699 A | * | 7/1980 | Moore | 356/70 |
| 4,952,055 A | * | 8/1990 | Wyatt | 356/73 |
| 4,993,832 A | * | 2/1991 | Pawliszyn | 356/128 |
| 5,347,358 A | * | 9/1994 | Nebe et al. | 356/128 |
| 5,694,210 A | * | 12/1997 | Newell et al. | 356/128 |
| 6,504,966 B2 | | 1/2003 | Kato et al. | 385/16 |
| 2005/0024629 A1 | * | 2/2005 | Pike | 356/128 |

OTHER PUBLICATIONS

"Silica Integrated Optical Circuits", edited by H. M. Presby, Section 2 "Fabrication", SPIE Milestone Series, vol. MS 125, pp. 43-149, 1986.

T. Fukano and I. Yamoguchi, "Simultaneous measurement of thicknesss and refractive indices of multilayers by a low-coherence confocal interference microscope", Opt. Lett., vol. 21, pp. 1942-1944, 1996.

G. J. Veldhuis, L.E. W. van Veen and P. V. Lambeck, "Integrated optical refractometer based on waveguide bend loss", IEEE J. Lightwave Technol., vl. 17, pp. 857-864, 1999.

D. C. Yin and Y. Inatomi, "Measurement of refractive index of GaP crystal over a large temperature range using interferometry", Cryst. Res. Technol., vol. 35, pp. 221-228, 2000.

T. Dennis, E. M. Gill and S. L. Gilbert, "Interferometric measurement of refractive-index change in photosensitive glass", Appl. Optics, vol. 40, pp. 1663-1667, 2001.

(Continued)

*Primary Examiner*—Gregory J. Toatley, Jr.
*Assistant Examiner*—Kara Geisel
(74) *Attorney, Agent, or Firm*—Sheppard, Mullin, Richter & Hampton LLP

(57) ABSTRACT

Methods and apparatuses for measuring the optical properties of solids, gels, and liquids are disclosed. The apparatuses may be constructed on miniature substrates using conventional semiconductor wafer and packaging processes. The substrates may be mass-produced on wafers, which are then diced to provide individual miniature substrates. High measurement precision, low-manufacturing costs, and other benefits are provided by the present inventions.

26 Claims, 10 Drawing Sheets

OTHER PUBLICATIONS

O. M. Efimov, L. B. Glebov and H. P. Andre, "Measurement of the induced refractive index in a photothermorefractive glass by a liquid-cell shearing interferometer", Appl. Optics, vol. 41, pp. 1864-1870, 2002.

A. L. Glebov, L. Huang, S. Aoki, M. G. Lee and K. Yokochi, "Two dimensional microlens arrays in silica-on-silican planar lightwave circuit technology", Journal of Microlithography, Microfabrication, & Microsystems, vol. 2, No. 4, pp. 309-318, 2003.

Metricon Corp., "Model 2010 Prism Coupler Application Notes Measuring Index Anisotropy of Free-Standing Polymer Films," www.metricon.com/appli6.htm, Jun. 29, 2004.

Brother Gregory Investigates, "Measuring Refractive Index," www.brooklyn.cuny.edu/bc/ahp/CellBio/RefIndex/RI.Main.html, Jun. 30, 2004.

* cited by examiner

METHODS AND APPARATUSES FOR MEASURING THE REFRACTIVE INDEX AND OTHER OPTICAL PROPERTIES OF LIQUIDS, GELS, AND SOLIDS

FIELD OF THE INVENTION

The present invention relates to methods and apparatuses for measuring the index of refraction of liquids, solids, and gels.

BACKGROUND OF THE INVENTION

There is a general interest in the art to characterize the index of refraction (also called refractive index, or RI) of the materials used in optical and opto-electronic systems. These materials include liquids, gels, and solids.

Index matching fluids (IMF) have been widely used in fiber optic applications in order to reduce the reflection losses between optical components. They can take the form of liquids or gels, each having a substantial range of viscosity. The refractive index is one of the most important properties of an 1 MF, and for some optical systems, knowledge of the precise value is absolutely critical. Precise determination of the refractive index of liquid substances is also desired in non-optical fields, such as in the food and oil industries since the refractive index is often correlated with other properties and since it can often provide an easier way of indirectly measuring those other properties.

A refractometer, a prism coupler, and an ellipsometer are three traditional apparatuses for measuring refractive index. In a refractometer, light is passed through a transparent block of solid material and the distance between the exit spot and a reference point is determined to evaluate the refractive index of the material. In a prism coupler, a prism is placed on top of a layer of the material to be measured, and the critical insertion angles, i.e., angles of the optical tunneling for various modes at the interface between the prism and the layer, are used to evaluate the refractive index of the thin film material. An ellipsometer relies on the polarization dependence of the light reflecting at an interface, and on the phase change, which depends on the refractive index of the material when the light travels through a layer of the material. More recently, a number of interferometric methods have been developed and applied to measure refractive index and/or its changes for various materials. All these methods require a solid piece of material, or at least a cured gel-like layer of material.

SUMMARY OF THE INVENTION

In making their invention, the inventors have recognized that there is no easy and inexpensive way of measuring the refractive index of liquids or gels with high accuracy.

A first invention of the present application encompasses apparatuses and methods for measuring the refractive index of liquids, gels, and liquids that can be changed to solids (e.g., curable liquid substances) by filling the same inside a lens structure (such as planar microlens structure in preferred embodiments) and measuring the beam width at distance away from the lens structure. The present invention enables measurements on both static specimens and dynamic specimens, the latter being, for example, a liquid material flowing through a planar microlens structure according to the present invention. Results obtained to date indicate that a system and method according to the present invention can achieve an absolute precision of at least $1 \times 10^{-4}$ in the refractive index. While this degree of accuracy is comparable to existing absolute-precision systems, apparatuses and methods according to the present invention can be implemented at far less cost than existing systems, and can provide greater degrees of flexibility in measuring specimens.

An exemplary apparatus for measuring the refractive index of a substance according to the first present invention comprises a substrate, a planar spreading lens disposed on the substrate, and a planar converging lens that is disposed on the substrate and that has a first surface facing the planar spreading lens and a second surface opposite to the first surface. A gap is located between the planar spreading lens and the planar converging lens, and is capable of receiving the substance whose refractive index is to be measured. A beam profiler is disposed opposite to the second surface of the planar converging lens, and spaced at a distance from the planar converging lens.

As a second invention of the present application, a lens structure with a gap for receiving a sample is provided. The lens structure enables a light beam to be deflected in relation to the refractive index of the sample. In a first set of implementations, the sample is placed at an angle with respect to the light beam in the lens structure. In another set of implementations, the lens structure comprises two lenses with optical axes that are angled with respect to one another.

As a third invention of the present application, a multi-lens structure for receiving two or more samples of the same material is provided. Each lens structure has a gap between two lenses, with at least two gaps being different in length. Optical properties of the two materials may be characterized over two different lengths of material, with lens components that are substantially matched in characteristics. The difference between samples may be used to estimate various properties of the material, such as optical loss (e.g., attenuation).

As a fourth invention of the present application, a lens structure is integrated on a substrate in close proximity to an optical device to monitor the properties of an optical material of the device during operation, such as over long periods of time. The lens structure has a gap between two lenses, with the gap being filled with the optical material of the device to be monitored. The monitoring may be used by control circuitry for the device to modify control signals to the optical device to compensate for changes in the properties of the devices optical material.

It is an objective of the present invention to provide an inexpensive method and apparatus for measuring the index of refraction of liquid, gels, and solids.

It is yet another object of the present invention to provide a compact apparatus for measuring the index of refraction of liquid, gels, and solids.

It is a further object of the present invention to provide methods and apparatuses for measuring the index of refraction of liquid, gels, and solids in the presence of magnetic fields, electric fields, temperature extremes, and other environmental conditions.

DETAILED DESCRIPTION OF THE INVENTION

Methods and apparatuses according to the present invention are first generally described before providing specific embodiments. A substance whose refractive index is to be measured is disposed between a first lens and a second lens. In preferred embodiments, the first lens is a spreading lens and the second lens is a converging lens. A light beam is passed through the spreading lens, the substance to be tested, and the converging lens, with the light beam exiting the converging lens into a medium of different refractive index, preferably lower (e.g., air). Taking into account the refractive index of this medium and the wavelength(s) of the light beam, and also the target range of refractive index for the substance, the refractive indices and geometries of the lenses are preferably designed such that exiting light initially converges, and then diverges with distance away from the converging lens. The beam width varies with the value of the refractive index of the substance (as measured in both of the converging and diverging sections), such that the refractive index may be estimated through comparison of the beam width to a previously-determined relationship between refractive index and beam width. The comparison may occur in either the converging section or the diverging section. The previously-determined relationship may be determined empirically, or by simulation, or by a combination of experiment and simulation, examples of which are provided below. The light is preferably monochromatic or has a relatively narrow range of wavelengths (e.g., 100 nm), but may comprise a full spectrum or partial spectrum (in which case an "average" refractive index may be obtained). The light may be coherent or incoherent.

The present invention may be practiced using conventional lenses, which have three-dimensional optical surfaces (like that of the surface of a ball), or may be practiced using lenses built upon planar substrates, with these lenses having two-dimensional optical surfaces rather than three-dimensional surfaces. These latter lenses are referred to herein as "planar lenses" since they are built upon planar substrates. Embodiments using planar lenses are presently preferred since they can be manufactured at lower costs and can be made in more compact dimensions, if so desired.

Figure 1:
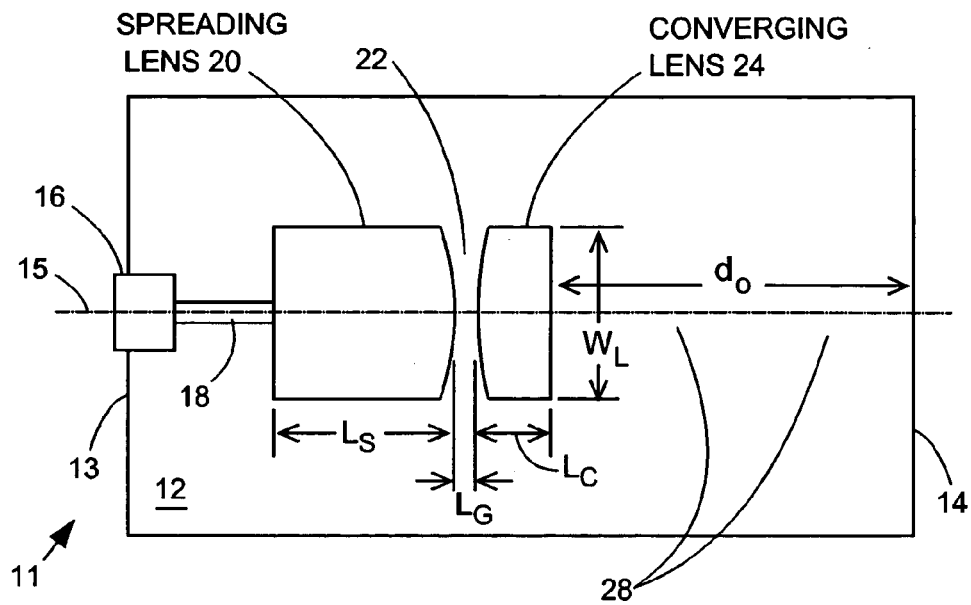
FIG. 1 shows a top plan view of an exemplary assembly embodiment according to the first present invention.
Figure 3:
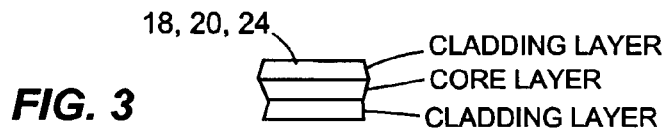
FIG. 3 shows a side view of the layer construction of the lenses and waveguide of the exemplary assembly embodiment shown in FIGS. 1 and 2 according to the present first invention.
Figure 2:
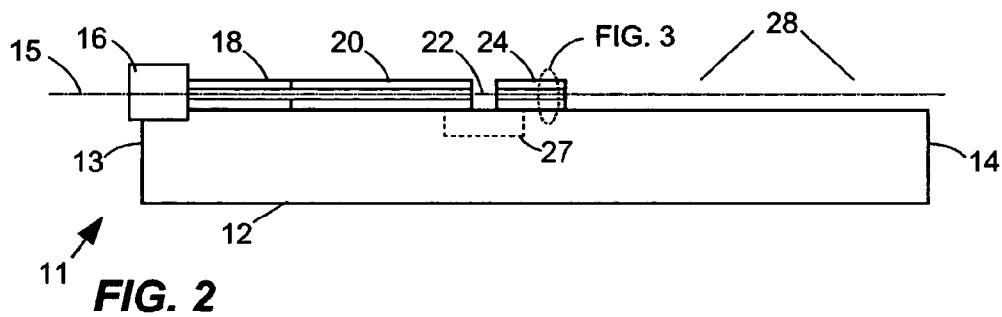
FIG. 2 shows a side view of the exemplary assembly embodiment of FIG. 1 according to the first present invention.

FIGS. 1-6 show various views of a first embodiment of an exemplary apparatus and method according to the present invention where planar lenses are used. The first embodiment is shown at reference number 10 in whole in FIG. 6. Common reference numbers are used in these figures to identify the elements of the apparatus. FIG. 1 shows a top plan view of an assembly 11 that holds a planar spreading lens 20 and a planar converging lens 24 on the top surface of a substrate 12. The lenses are held in a fixed relationship to one another with a gap 22 between them. Substrate 12 has a first side 13, and a second side 14 opposite to the first side 13. Light is preferably provided to spreading lens 20 by way of a ridge waveguide 18, which in turn can receive the light by a source integrated onto substrate 12 or by a source external to substrate 12. FIG. 1 shows an embodiment where the light source is coupled from an optical fiber to waveguide 18 using any kind of fiber interconnect, which is designated in FIG. 1 by reference number 16. Fiber interconnect 16, when used, is preferably disposed near or at the first side 13. Other optical coupling arrangements may be use, such as optical focusing of light onto the left side of lens 20, which can be readily done when using the fixture (50) described below in greater detail with regard to FIG. 9. If using an integrated light source, the light source 5 would be moved to the position of fiber interconnect 16 in FIG. 6. Converging lens 24 is spaced from side 14 by distance $D_0$, which is explained below in greater detail. Between converging lens 24 and side 14, there is disposed an exit medium 28, which is typically air having an index of refraction of 1.0003. The area on the top surface of the substrate 12 located between lens 24 and the second side 14 and the exit medium are free of obstructions to the wavelengths of light being emitted by source 5. In this figure, and in FIGS. 2 and 4-6, the center optical axis is denoted by reference number 15. The center optical axis 15 is also known as the principal optical axis.

FIGS. 1-6 show various views of a first embodiment of an exemplary apparatus and method according to the present invention in which planar lenses are used. The first embodiment is shown in whole at reference number 10 in FIG. 6. Common reference numbers are used in these figures to identify the elements of the apparatus. FIG. 1 shows a top plan view of an assembly 11 that holds a planar spreading lens 20 and a planar converging lens 24 on the top surface of a substrate 12. The lenses are held in a fixed relationship to one another with a gap 22 between them. Substrate 12 has a first side 13, and a second side 14 opposite to the first side 13. Light is preferably provided to spreading lens 20 by way of a ridge waveguide 18, which in turn can receive the light by a source integrated onto substrate 12 or by a source external to substrate 12. FIG. 1 shows an embodiment in which the light source is coupled from an optical fiber to waveguide 18 using any kind of fiber interconnect, which is designated in FIG. 1 by reference number 16. Fiber interconnect 16, when used, is preferably disposed near or at the first side 13. Other optical coupling arrangements may be used, such as optical focusing of light onto the left side of lens 20, which can be readily done when using the fixture (50) described below in greater detail with regard to FIG. 9. If using an integrated light source, the light source 5 would be moved to the position of fiber interconnect 16 in FIG. 6. Converging lens 24 is spaced from side 14 by distance $D_0$, which is explained below in greater detail. Between converging lens 24 and side 14, there is disposed an exit medium 28, which is typically air having an index of refraction of 1.0003. The area on the top surface of substrate 12 located between lens 24 and second side 14 and the exit medium is free of obstructions to the wavelengths of light being emitted by source 5. In this figure, and in FIGS. 2 and 4-6, the center optical axis is denoted by reference number 15. The center optical axis 15 is also known as the principal optical axis.

Referring back to FIG. 1, spreading lens 20 has a length $L_S$ parallel to axis 15, converging lens 24 has a length $L_C$ parallel to axis 15, and both lenses have a width $W_L$ perpendicular to axis 15. Gap 22 has a length $L_G$, as measured at axis 15 (center of width $W_L$). Spreading lens 20 has a first side coupled to waveguide 18, and a second side opposite to the first side and having a convex surface. With waveguide 18 coupled to spreading lens 20 directly, and with the cores of waveguide 18 and spreading lens 20 having the same effective index of refraction, the first side of spreading lens 20 may have a surface of any shape. Converging lens 24 has a first side with a convex surface, and a second side opposite to the first side. The second side of converging lens 24 faces exit medium 28, and typically has a flat surface, but may have a concave shape or a convex shape since the curvatures of both sides of converging lens 24 may be selected to provide a desired degree of convergence.

Figure 4:
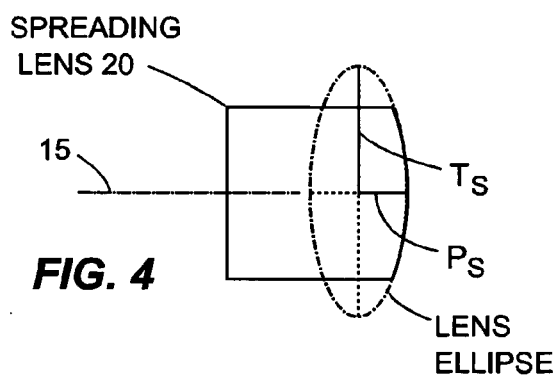
FIG. 4 shows an exemplary ellipsoidal curvature of the first lens according to the first present invention.
Figure 5:
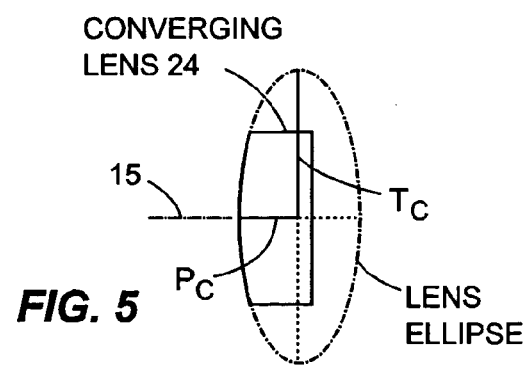
FIG. 5 shows an exemplary ellipsoidal curvature of the second lens according to the first present invention.

Referring to FIGS. 4 and 5, each of the curvatures of lenses 20 and 24 may be mathematically specified by the contour of an ellipse, which is referred to herein as the lens ellipse. A generic ellipse has a major axis "a" disposed along the x-axis of the coordinate system, a minor axis "b" disposed along the y-axis of the coordinate system, and a mathematical definition of: $(x^2/a^2)+(y^2/b^2)=1$. By convention, the major axis is along the longer dimension of the ellipse, with the longer dimension being $2a$ and the shorter dimension being $2b$. In our case, without loss of generality, we prefer to align center optical axis 15 with the x-axis of the coordinate system (i.e., to be parallel and co-linear to the optical axis 15). Since lenses 20 and 24 will sometimes have their longer dimensions oriented transverse (perpendicular) to center optical axis 15, we will adopt a new convention for defining the ellipse axes rather than use the "a" and "b" axes convention. In our convention, the ellipse axis which is parallel to optical axis 15 will be generally denoted as the P-axis with a value "P", and the ellipse axis which is transverse to optical axis 15 will be generally denoted as the T-axis with a value "T." For spreading lens 20, a subscript "S" will be added to these values (e.g., $P_S$ and $T_S$); for converging lens 24, a subscript "C" will be added to these values (e.g., $P_C$ and $T_C$). With these definitions, the curvature of spreading lens 20 may be defined by the mathematical equation: $(x^2/P_S^2)+(y^2/T_S^2)=1$, and the curvature of converging lens 24 may be defined by the mathematical equation: $(x^2/P_C^2)+(y^2/T_C^2)=1$. The diameters of lenses 20 and 24 along the P-axes are $2P_S$ and $2P_C$, respectively; and the diameters of lenses 20 and 24 along the T-axes are $2T_S$ and $2T_C$, respectively.

As described below in greater detail, the values of $L_S$, $L_C$, $L_G$, $W_L$, and the curvatures of the lenses (e.g., $P_S$, $T_S$, $P_C$, $T_C$) are selected for a desired test range of refractive index for the substance being measured, and are selected to provide a beam width that monotonically varies as a function of the substance's refractive index within the test range. This usually results in the light having a beam width of at least 50 μm as it exits the second surface of converging lens 24, and more typically results in the light having a beam width of at least 100 μm to at least 150 μm at this point (beam widths of at least 200 μm are possible). An exemplary embodiment will also be given. While it is preferred that the P-axes of the lenses be aligned with center optical axis 15, it may be appreciated that embodiments can be constructed with the P-axes offset and/or rotated with respect to center optical axis 15. In addition, while lenses with ellipsoidal curvatures ($P_S \neq T_S$, $P_C \neq T_C$) are presently preferred, it may be appreciated that embodiments can be constructed with one or both lenses having circular curvatures. The lenses may also have different widths $W_L$, may also have different layer constructions, and may also have different effective core refractive indices.

Figure 6:
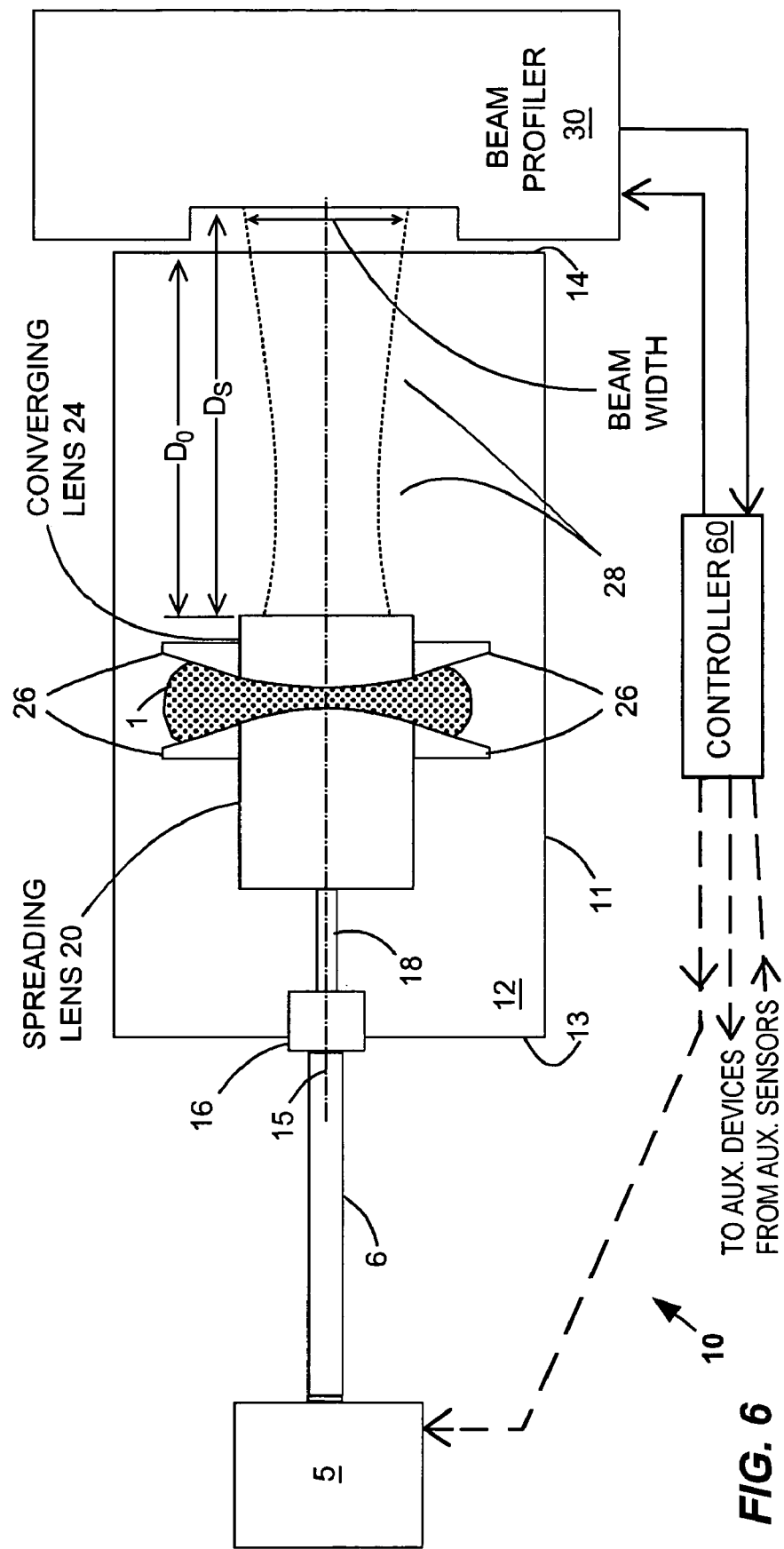
FIG. 6 shows a top view of an exemplary apparatus according to the first present invention.

FIG. 6 is a top plan view showing assembly 11 disposed between a light source 5 and a beam profiler 30. Light source 5 is coupled to ridge waveguide 18 by way of optical fiber 6, which is held in place relative to waveguide 18 by fiber interconnect 16. FIG. 6 also shows a substance 1, whose refractive index is to be measured, disposed within gap 22. Also shown in FIG. 6 are capillary guides 26 disposed at the edges of lenses 20 and 24. Capillary guides 26 may comprise ridges of material that may be formed during the formation of lenses 20 and 24 (with the same material), or may be formed or attached after lenses 20 and 24 have been formed. Guides 26 provide an opening to substance 1 that is wider than distance $L_G$, and act to direct substance 1 to the faces of lenses 20 and 24 by capillary action. While two pairs of capillary guides are shown (one pair on either side of optical axis 15), one pair on one side of optical axis 15 would be sufficient to draw a liquid into lens gap 22. In some implementations, such as when $L_G$ is relatively wide, guides 26 are not needed. In still other implementations that do not need guides 26, a recess may be formed in substrate 12 in the general area where substance 1 is to be disposed, including the areas between the guides 26 shown in FIG. 6. The recess may take the general outline of substance 1 shown in FIG. 6, and may have distal edges that are wider than distance $L_G$, thereby acting to direct substance 1 to the faces of lenses 20 and 24 by capillary action. An exemplary recess is shown at 27 in FIG. 2, as outlined at one of its distal edges. While guides 26 are not needed for embodiments that use the recess, they nonetheless may be incorporsted onto the substrate.

The beam profiler 30 has at least the ability to measure a width of the light beam presented to its optical capture window, and is oriented to measure the beam width in a direction which is parallel to the top surface of substrate 12. Many beam profilers are capable of measuring the beam width in two orthogonal directions, but this is not needed to make and use the present invention. Most beam profilers define the beam width as the distance between two points on either side of the beam's maximum intensity point (i.e., the center point), with the two points having intensities equal to a certain fraction of the beam's maximum intensity value.

Typically, the value of that certain fraction is $1/e^2 = 0.135335$, where e is the base of the natural logarithm (e=2.71 828. . . ). In other words, the light intensity at these two side points is equal to $1/e^2$ (0.135335) multiplied by the maximum beam intensity (at the center point). Instead of using the fraction of $1/e^2$, some profilers use the fraction ½ (the so-called "full-width, half maximum" definition), or allow the user to define the fraction. In addition, some profilers may define the width as the distance from the maximum intensity (at center) to one of the side points (or as the average of the two distances to the side points), but these definitions are not conventional. Nonetheless, the present invention may be practiced with any definition of the beam width. The inventors have practiced the present invention using a BeamScan® profiler manufactured by Photons, Inc. This profiler is a slit-based real-time beam profiler, and uses a large area monolithic detector that collects light transmitted through a slit aperture as it passes through the beam.

FIG. 6 also shows the initial convergence, then divergence, of the beam width as the light travels from the converging lens to the beam profiler over a distance Ds. The profile of the beam varies with the refractive index of the substance to a degree that can be readily detected by beam profiler 30. At a distance of Ds=35 mm, a typical beam width is around 250 µm, and varies by approximately 30 µm for a change of $5 \times 10^{-4}$ in the refractive index of substance 1.

Figure 7:
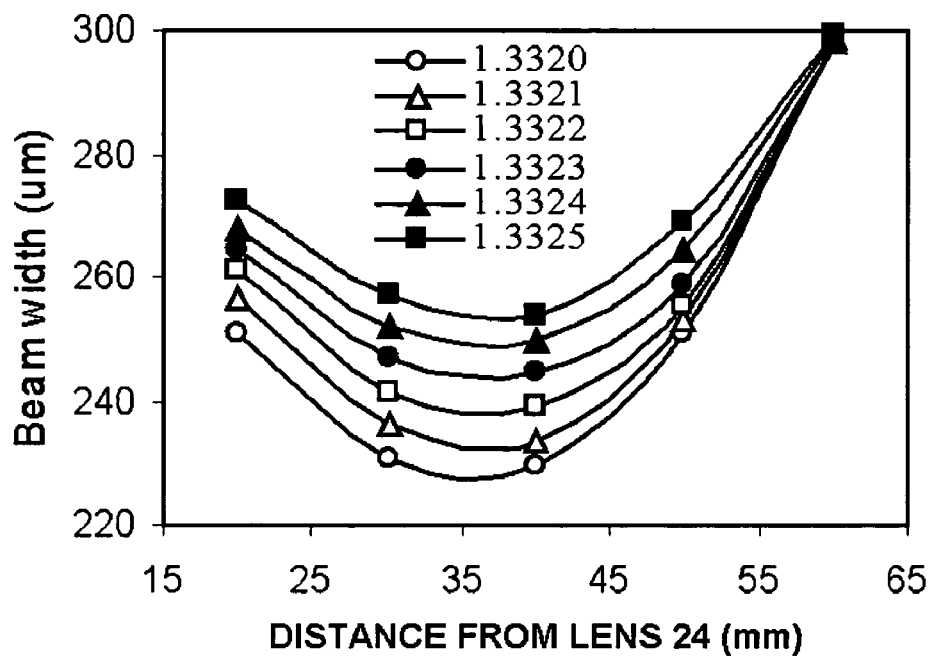
FIG. 7 shows a graph of beam width versus refractive index and distance between lens and profiler according to the first present invention.

The variation in beam width with respect to distance Ds and refractive index of the substance for an exemplary embodiment is shown in FIG. 7. The parameters for this exemplary embodiment are provided below in Example 1. The curves in FIG. 7 may be generated by optical simulation software well known to the art (such as OptiBPM® by Optiwave Corporation), or may be measured empirically by using several substances of known refractive index, and by placing the profiler's scan head on a carriage that is moved on an automated rail, with the profiler measuring the beam width as it is moved away from the converging lens (in this case, $D_0$ is set at a small value, such as 1 mm). In the empirical approach, the beam propagation profile is preferably measured three or more times to avoid errors due to misalignment of the system, and the final curves are averaged. The beam width is then calculated after subtracting the background intensity.

Figure 8:
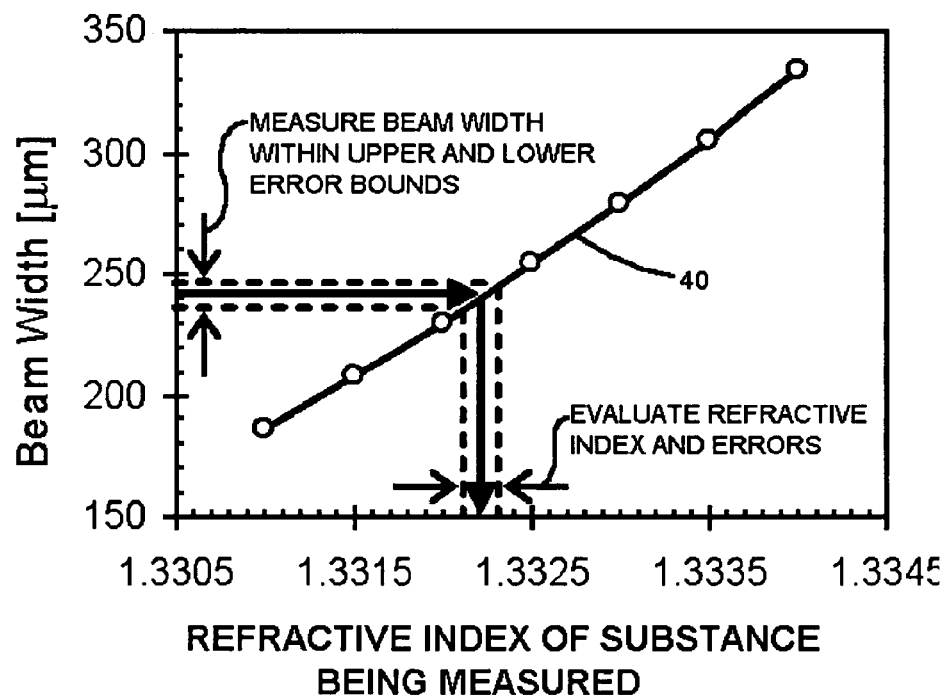
FIG. 8 shows a relationship between beam width and refractive index of the substance being measured according to the first present invention.

By extracting data along a vertical line in FIG. 7, such as along the vertical line of "distance from lens"=35 mm, a relationship between beam width and refractive index of the substance can be generated (for that distance). Such a relationship is shown at 40 in FIG. 8. The vertical line used to extract data from FIG. 7 is preferably located near the greatest divergence in the data curves, and the lens system components 20, 22, and 24 are preferably designed to provide a beam width of at least 100 µm in this area. Relationship 40 is a monotonic relationship that relates the measured beam width (at a given distance $D_s$) to the refractive index of the substance 1 being measured. By taking the measured beam width, one may draw a horizontal line across the graph, with the horizontal line intersecting the beam-width axis at the measured value of beam width. The horizontal line intersects relationship 40 at a point, and a vertical line may be drawn from this point down to the refractive-index axis. The intersection of the vertical line with the refractive-index axis gives the corresponding value of the substance's refractive index. In general, profiler 30 has error in its measurement process. For example, when using BeamScan profiler® manufactured by Photons, Inc. for profiler 30, the beam width can be measured with an accuracy better than ±2%, which is approximately ±5 µm for a mean beam width of 250 µm. As shown in FIG. 8, one may bracket the measure value with dashed lines representing the upper and lower error bounds. These dashed lines intersect relationship 40, and corresponding vertical dashed lines to the refractive-index axis may be drawn in order to generate error bounds on the refractive index value.

In preferred embodiments, a mathematical form for relationship 40 is generated, and the above process of finding refractive index values from measured beam width values is done by evaluating the mathematical form. In other words, from the data, a mathematical relationship can be generated which gives the refractive index as a function of a variable, whose value is set to equal the measured beam width. The mathematical form can have many embodiments. For example, in one such embodiment, a quadratic equation having the form $RI = a*BW^2 + b*BW + c$, where RI is a variable representing the refractive index and BW is a variable representing measured beam width, can be fitted to the data using well known least-squares fitting methods. In a second such embodiment, the mathematical form may comprise a set of linear equations of the form $RI = b_i * BW + c_i$, with each linear equation connecting two data points and being used to provide the relationship between those two data points. In a third such embodiment, the mathematical form may comprise a mathematical spline function, many forms of which are well-known to the mathematics art. Other mathematical functional forms are possible, and the present invention is not limited to the examples provided above.

Apparatus 10 may include a controller 60 that performs the tasks of instructing beam profiler 30 to measure the beam width BW, and to compute the refractive index from the measured beam width BW and relationship 40. Signal lines, either wired or wireless, are coupled between controller 60 and beam profiler 30 to assist in executing these tasks. In addition, signal lines, either wired or wireless, may be coupled between controller 60 and a user interface device, such as a keyboard and computer terminal. The latter elements are generally indicated in FIG. 6 as "AUX. devices" and "AUX. sensors", where "AUX." is a shorthand notation for auxiliary, and where "AUX. sensors" include keyboard, key pads, buttons and the like.

Figure 9:
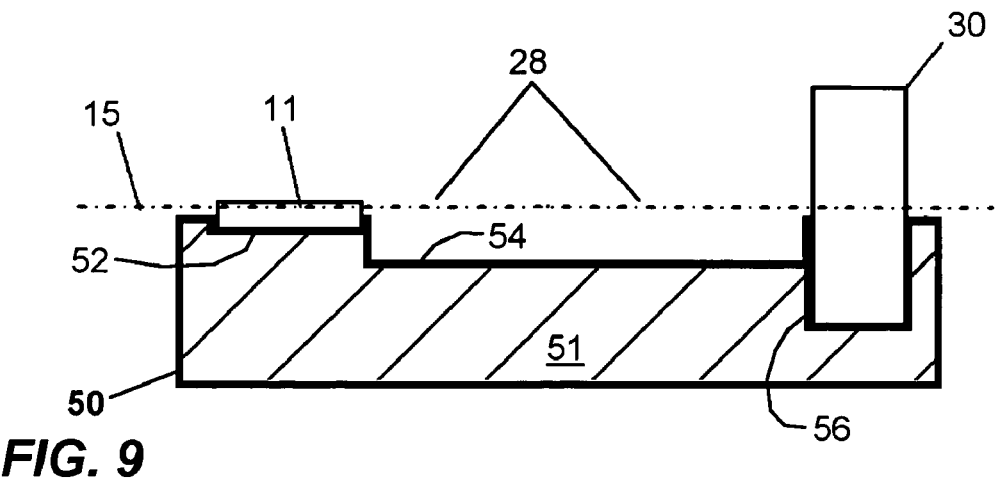
FIG. 9 shows an exemplary fixture and its use according to the first present invention.

A number of approaches may be used to position assembly 11 from beam profiler 30 to achieve the desired separation distance $D_S$. In one approach, distance $D_0$ of assembly is set substantially equal to $D_S$, and the assembly is abutted against the protective facing of the optical capture window of profiler 30. To compensate for the small distance between the protective facing and the optical capture window of the profiler, the value of $D_0$ is to be less than $D_S$ by this small distance. In preferred embodiments in this first approach, since light exiting lens 24 can reflect off substrate 12 and affect the measured beam profile, the top surface of substrate 12 in the area between lens 24 and side 14 is treated so as to be light-absorbing, such as by coating it with a light-absorbing material. In a second approach, assembly 11 is constructed with distance $D_0$ set to a value near zero, and assembly 11 is placed in a fixture 50, as shown in FIG. 9. Fixture 50 comprises a frame or substrate 51, a first retainer 52 disposed on frame/substrate 51 for holding substrate 11, a second retainer 56 disposed on frame/substrate 51 for attaching to the optical capture element of profiler 30 (or in some cases holding the optical capture element of profiler 30 depending upon the type of profiler used), and an optically-cleared area 54 disposed between retainer 52 and 56. Fixture 50 substantially sets (i.e., substantially fixes) the distance between lens 24 and the optical capture window of profiler 30 to the desired value of $D_S$. As one exemplary embodiment, each of elements 52, 54, and 56 may comprise a respective recess in a substrate 51 (as shown in FIG. 9). In other embodiments, first and second retainers 52 and 56 may comprise holders (e.g., clamps) that are attached to a common frame 51 and elevated above the body of the frame to provide optically-cleared area 54.

Thus, to summarize, a substance 1 is disposed in gap 22 of assembly 11. Assembly 11 is aligned with beam profiler 30 with the desired separation distance $D_S$. When not using fixture 50, the value of $D_0$ may be set to achieve the desired value of $D_S$ when side 14 is contacted to the face of beam profiler 30. When using fixture 50, $D_0$ is set to a value that enables assembly 11 to be received by retainer 52. Light is then coupled to waveguide 18 from light source 5. Using profiler 30, the width of the exit beam is measured (several measurements may be taken and then averaged), and the refractive index of substance 1 is estimated with a high degree of accuracy from the measured beam width and relationship 40.

EXAMPLE 1

Figure 10:
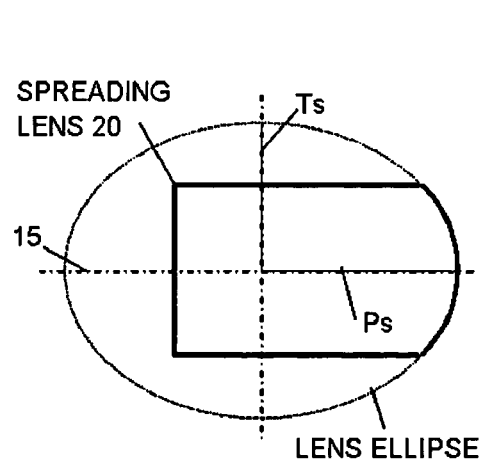
FIGS. 10 and 11 show exemplary lens ellipses according to the present inventions.
Figure 11:
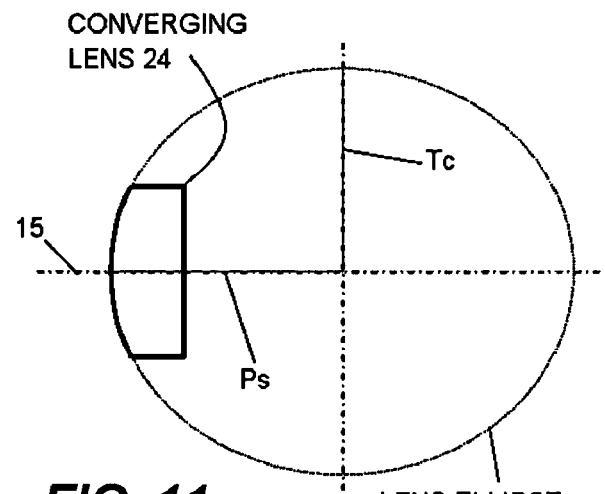

Table 1 provides exemplary parameters for assembly 11 in the case of measuring refractive index in the range of 1.330 to 1.336 using light having a wavelength of 1550 nm. FIGS. 10 and 11 show the relative shapes and curvatures of lenses 20 and 24 for this exemplary embodiment.

TABLE I

| | |
|---|---|
| Refractive Index Range for the Substance | 1.330 to 1.336 |
| Wavelength of source light | 1550 nm |
| Thickness of lens core layer | 5 μm |
| Refractive index of core layer | 1.4553 |
| Thickness of lens bottom cladding layer | 15 μm |
| Thickness of lens top cladding layer | 7.5 μm |
| Refractive index of cladding layers | 1.444 |
| Effective core refractive index | 1.451974 |
| Width of lenses 20 and 24 | $W_L$ = 650 um |
| Length of spreading lens 20 | $L_S$ = 2000 μm |
| Curvature of spreading lens 20 | $P_S$ = 944 μm |
| | $T_S$ = 469 μm |
| Length of converging lens 24 | $L_C$ = 450 μm |
| Curvature of converging Lens 24 | $P_C$ = 2143 μm |
| | $T_C$ = 1066 μm |
| Gap length between lenses | $L_G$ = 50 μm |
| Refractive Index of exit medium | 1.0003 (air) |

To measure other ranges of refractive index, it is best to construct lens 20 and 24 to provide a relationship 40 with good slope characteristics (i.e., not too shallow, and with a good divergence pattern as shown in FIG. 7). After selecting a desired RI measurement range for assembly 11, one of ordinary skill in the art, in view of the teaching of this disclosure, can employ commercially available optical simulation software well known to the art (such as OptiBPM® by Optiwave Corporation) to select the parameters of lenses 20 and 24 and the length of gap 22 to provide for a relationship 40 with good characteristics for the desired range. As some basic guidance, we provide the following qualitative guidance. To measure a refractive index range that is greater than that targeted by Example 1, such as a range around 1.6 instead of 1.33, the transverse axis of one or both of the lenses 22 and 24 ($T_S$ and/or $T_C$) should be reduced. To measure a refractive index range that is less than that targeted by Example 1, such as a range around 1.1 instead of 1.33, the transverse axis of one or both of the lenses 22 and 24 ($T_S$ and/or $T_C$) should be increased.

The above-described methods and apparatus can be used to determine the absolute value of the refractive index for almost any liquid, gel or curable liquid gel with an absolute precision of at least $1 \times 10^{-4}$ when using a typical beam profiler. The above methods and apparatuses are simple, inexpensive, and rugged (durable), and, thus, can be easily reproduced in laboratory and manufacturing conditions. We illustrate each below. The methods and apparatuses can also be easily applied to determine the variations in the refractive index of a substance caused by a number of factors, including temperature, wavelength, electric field, magnetic field, and humidity.

Referring to FIG. 6, refractive index can be measured as a function of wavelength by using a wavelength-tunable light source for light source 5. In this embodiment, controller 60 may be used to control light source 5, and may step through a plurality of different light wavelengths while it controls beam profiler 30 to measure the beam width BW at each selected light wavelength. In this manner, one may assemble a correlation of refractive indices for substance 1 at a plurality of different light wavelengths, and then construct from this a relationship between refractive index and wavelength, which may be expressed by mathematical formulas and/or graphs.

Figure 12:
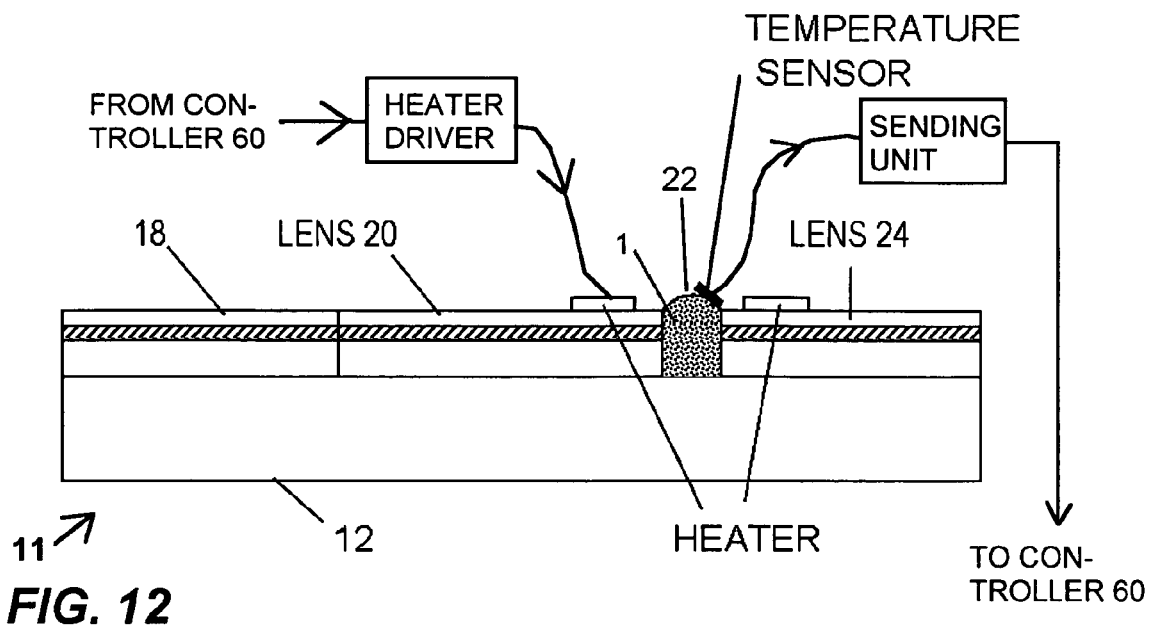
FIGS. 12 and 13 show exemplary assemblies which facilitate the measurement of temperature dependency according to the present inventions.

As to measuring temperature dependency, there are a number of possible configurations that may be used. FIG. 12 shows an implementation of assembly 11 that includes a heater element driven by a heater driver, and a temperature sensor which is coupled to a temperature sending unit. The heater element may comprise highly resistive material that is fed with power from the heater driver, and the heater driver receives instructions from controller 60 (shown in FIG. 6). The heater element may be disposed on one or both of lenses 20 and 24, in close proximity to lens gap 22. There are several materials suitable for this purpose and that are well known to the art. The temperature sensor may comprise any of the well-known materials used for temperature sensors; these materials generally have large temperature coefficients (large charge in resistor for a change in temperature). The temperature sensor is coupled to a sending unit, which conveys a measured temperature value to controller 60. It is preferred in this embodiment that the temperature sensor be separately removable from assembly 11 so that it may be used for other assemblies. However, it is possible to integrate the temperature sensor on assembly 11, such as at the bottom of lens gap 22, or on top of one or both of lenses 20 and 24.

Controller 60 shown in FIG. 6 may be configured to control the application of power to the heater element, and configured to read the temperature value sensed by the temperature sensor. Controller 60 may be further configured to adjust the temperature of substance 1, as measured by the temperature sensor, at a plurality of temperature points, and to control beam profiler 30 to measure the beam width BW at each such temperature point. As another approach, the heater element may be configured to gradually ramp up the temperature above room temperature (20° C.) (or ramp down the temperature from a previously set high value, thereby cooling the device by allowing the environment to extract heat from substance 1 and the substrate), and controller 60 may be configured to monitor the temperature sensed by the temperature sensor, and to then instruct beam profiler 30 to measure the beam width BW at selected temperature points as they are encountered, or at selected time points during the ramp (so that the time points have different temperature values). As yet another approach, beam profiler 30 may be configured to provide periodic measured values of beam width BW to controller 60, the heater element may be configured to ramp up (or down) the temperature independent of the ramping action of the heater, and controller 60 may be configured to periodically read the output of the temperature sensor when it receives a measured beam width. In each of these embodiments, a correlated list of refractive indices for substance 1 measured at different temperatures can be constructed. From this, a relationship between refractive index and temperature can be constructed, which may be expressed by mathematical formulas and/or graphs. The several above embodiments demonstrate that there are a number of ways of assembling the correlated list of measured refractive index and temperature.

Figure 13:
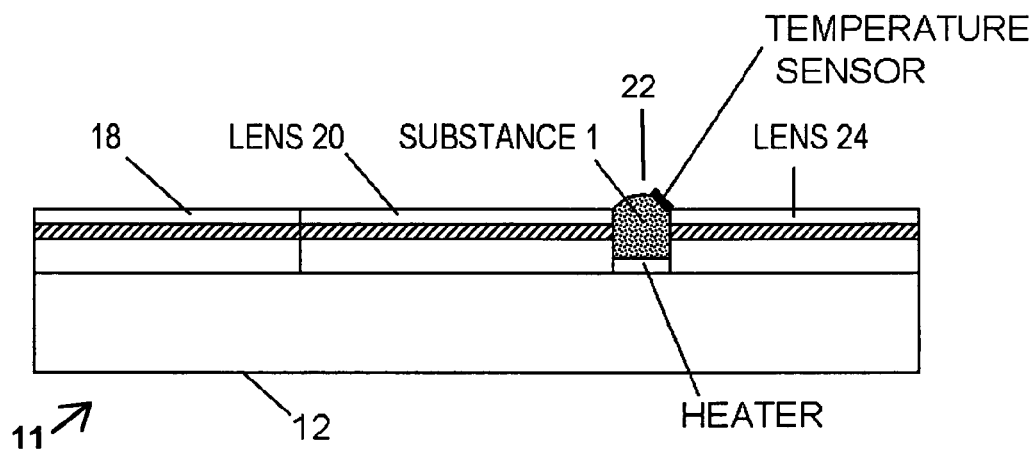

FIG. 13 shows another implementation of assembly 11 where temperature may be measured. In this implementation, the heater element (which may be of the same material as above) is formed on the bottom of lens gap 22. The temperature sensor may be of the same constructions as described above (e.g., separately removable from assembly 11, or integrated on assembly 11, such as on top of one or both of lenses 20 and 24). For visual simplicity, the heater driver and sending unit have not been shown in FIG. 12, but can be used in this embodiment. Any of the above-described methods of assembling the correlated list of measured refractive indices and temperature may be used with this embodiment. Still other embodiments for measuring the temperature dependence of the refractive index of substrate 1 can be used. For example, any of the above-described embodiments may be modified by using a heated chamber or heat lamp as a source of heat instead of the heater elements shown in FIGS. 12 and 13.

Figure 14:
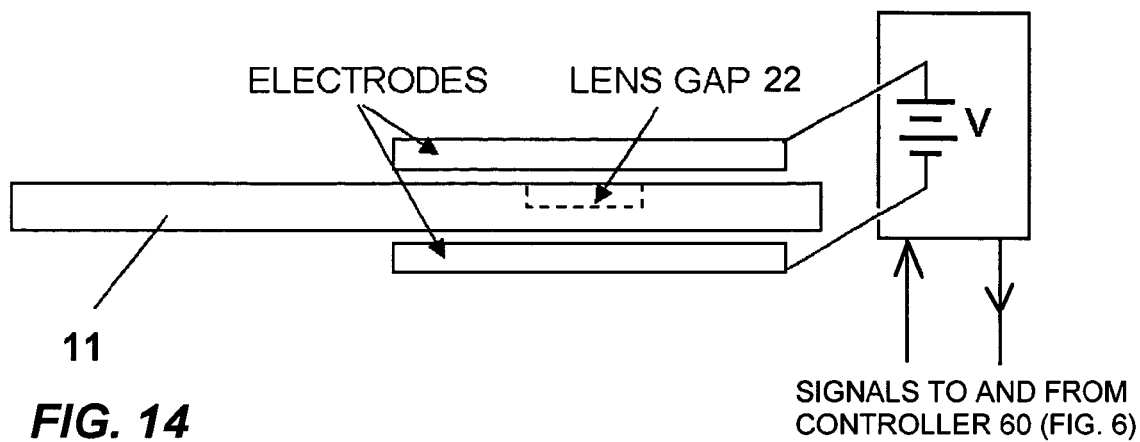
FIG. 14 shows an exemplary configuration which facilitates the measurement of electric-field dependency according to the present inventions.

FIG. 14 shows an embodiment where the electric field dependency of the refractive index of substance 1 may be measured. In this embodiment, two electrodes are positioned above and below assembly 11, respectively, with the two electrodes being spaced at a known distance from each other. Assembly 11 retains its optical set-up to source 5 and beam profiler 30, such as shown in FIG. 6. A voltage from a power source is applied between the two electrodes to create an electric field between the electrodes, which passes through substance 1 and assembly 11. From basic electromagnetic relationships well known to the art (e.g., Gauss's law), a relationship between the electric field present in substrate 1 as a function of voltage on the electrodes may be determined, taking into account the thickness of assembly 11, the electrode spacing distance, and the relative dielectric constants of assembly 11 and substance 1. In some embodiments, the air gaps may be eliminated, in which case the relationship can simplified as the electric field being substantially equal to the applied voltage divided by the thickness of assembly 11. As one such embodiment, a conductive material may be formed on the back surface of assembly 11 as one of the electrodes, and a top electrode may be directly pressed against the top surface of assembly 11 after substance 1 has been disposed in lens gap 22.

A number of approaches may then be used to assemble a correlated list of measured refractive indices of substance 1 and applied electric field. For example, controller 60 may have one of its control outputs coupled to the voltage source to direct the selection of specific voltages applied to the electrodes, while it instructs beam profiler 30 to measure the beam width at selected voltages. In other examples, the voltage source may be configured to vary its voltage in a pattern, such as in a sinusoidal pattern or triangular-wave pattern, and the controller may be configured to have a sensing input coupled to the voltage source to receive its current voltage value (or a voltage sensor device may be used instead). In this embodiment, controller 60 may instruct beam profiler 30 to measure the beam width when specific voltage levels are reached or when specific time points occur, or controller 60 may be configured to receive periodic beam width measurements from profiler 30, and correlate these measurements in time with the measured voltage values it receives. Although the control structure of each of the above embodiments is different, controller 60 is able to assemble a correlated list of measured beam widths and voltage levels, and from this a correlated list of refractive indices of substance 1 and electric field can be generated. From this, a relationship between refractive index and electric field can be constructed, which may be expressed by mathematical formulas and/or graphs.

Figure 15:
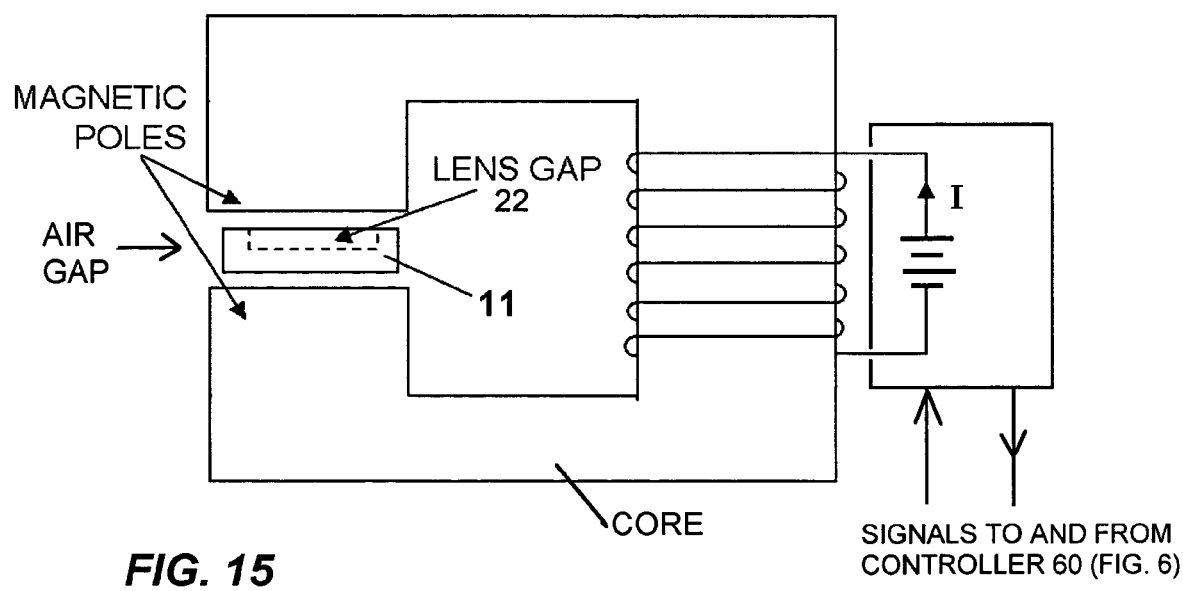
FIG. 15 shows an exemplary configuration which facilitates the measurement of magnetic-field dependency according to the present inventions.

FIG. 15 shows an embodiment where the magnetic field dependency of the refractive index of substance 1 may be measured. In this embodiment, a coil winding disposed around a ferromagnetic C-shaped core having two opposing magnetic poles and an air gap between them is used to generate a magnetic field. Assembly 11 is disposed within the air gap of the core, while retaining its optical setup to source 5 and beam profiler 30, such as shown in FIG. 6. (This may be easily accomplished by positioning the core in a plane that is transverse to the optical axis 15.) A current from a power source is applied to the coil winding to create a magnetic field between the magnetic poles, which passes through the air gap, substance 1 and assembly 11. The magnitude of the magnetic field may be varied by varying the magnitude of the applied current. In general, the permeabilities ($\mu$) of assembly 11 and substance 1 will be the same as that of air ($\mu_o$), and thus the magnetic field will be substantially uniform within the air gap. The magnetic field strength may be measured with a magnetic field sensor (e.g., a Hall-effect device) at the same time that the refractive index of substance 1 is being measured. As another approach, before measuring refractive index, the magnetic field strength may be measured, or otherwise determined, as a function of the applied current to construct a correlation table or relationship which provides the magnetic field strength as a function of applied current. While the use of a ferromagnetic core (of any shape) is preferred, it may be appreciated that it is not required, and that a coil alone may be used.

A number of approaches may then be used to assemble a correlated list of measured refractive index of substance 1 and applied magnetic field. For example, controller 60 may have one of its control outputs coupled to the current source to direct the selection of specific current to the coil winding (which generates corresponding specific magnetic fields), while it instructs beam profiler 30 to measure the beam width at selected voltages. In other examples, the current source may be configured to vary its current in a pattern, such as in a sinusoidal pattern or triangular-wave pattern, and the controller may be configured to have a sensing input coupled to the current source to receive its current value (or a current sensor or magnetic field sensor may be used instead). In this embodiment, controller 60 may instruct beam profiler 30 to measure the beam width when specific current levels are reached or when specific time points occur, or controller 60 may be configured to receive periodic beam width measurements from profiler 30, and correlate these measurements in time with the measured current values (or magnetic field strength values) it receives. Although the control structure of each of the above embodiments is different, controller 60 is able to assemble a correlated list of measured beam widths and current levels (or magnetic field strength values), and from this can generate a correlated list of refractive indices of substance 1 and magnetic field.

Thereform, a relationship between refractive index and magnetic field can be constructed, which may be expressed by mathematical formulas and/or graphs.

Figure 16:
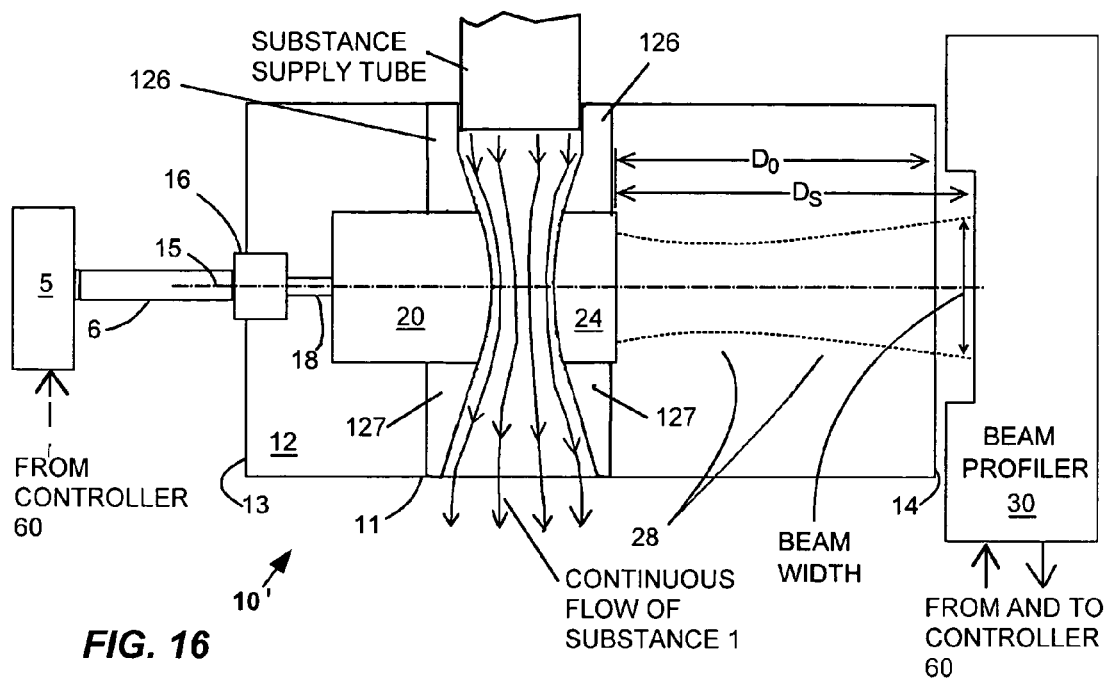
FIG. 16 shows an exemplary configuration which facilitates the measurement of time dependency (dynamic measurement) according to the present invention.

We have illustrated the above examples for cases in which substance 1 is disposed in lens gap 22 in a static manner. Substance 1 may be in liquid form, gel form, or may be solidified into a solid form after initially being disposed in lens gap 22 as a liquid or gel. In many manufacturing processes, there is a need to measure the refractive index of a flow of liquid material, such as to ensure the quality of the product. For example, in some food processing operations, it is important to monitor the sugar content of a liquid ingredient as it is being processed. The refractive index of the liquid ingredient has a monotonic relationship to the refractive index of the liquid. Thus, the invention may be used to measure the sugar content of the liquid ingredient by measuring the refractive index. This may be done real-time and in situ, by diverting a small amount of the stream of the liquid ingredient and passing it through lens gap 22. Such a setup is illustrated in FIG. 16. In order to facilitate the flow-through of the liquid, the lens gap distance LG is increased to 150 μm from 50 μm, and the curvature of the converging lens is changed (Pc=2278 μm, and Tc=1132 μm). The parameters of this second embodiment are provided in Table II. In addition, guides 26 are replaced by a tube interface 126 which receives a supply tube and fixes it to substrate 11, and exit guides 127, which direct the fluid away from the assembly. In operation, the supply tube provides a continuous sample of the substance to be measured, and controller 60 may be configured to periodically direct beam profiler 30 to measure the beam width, and from that generate a measured value for the refractive index of the substance.

TABLE II

| | |
|---|---|
| Refractive Index Range for the Substance | 1.330 to 1.336 |
| Wavelength of source light | 1550 nm |
| Thickness of lens core layer | 5 μm |
| Refractive index of core layer | 1.4553 |
| Thickness of lens bottom cladding layer | 15 μm |
| Thickness of lens top cladding layer | 7.5 μm |
| Refractive index of cladding layers | 1.444 |
| Effective core refractive index | 1.451974 |
| Width of lenses 20 and 24 | $W_L$ = 650 um |
| Length of spreading lens 20 | $L_S$ = 2000 μm |
| Curvature of spreading lens 20 | $P_S$ = 944 μm |
| | $T_S$ = 469 μm |
| Length of converging lens 24 | $L_C$ = 450 μm |
| Curvature of converging Lens 24 | $P_C$ = 2278 μm |
| | $T_C$ = 1132 μm |
| Gap length between lenses | $L_G$ = 150 μm |
| Refractive Index of exit medium | 1.0003 (air) |

The present invention can be implemented using silica-on-silicon planar lightwave circuit technology, which combines thermal oxidation of Si, chemical vapor deposition (CVD) of doped oxide layers, and reactive ion etching (RIE) of deep trenches. The present invention can also be applied in less expensive polymer-on-substrate lightwave circuit technology, which forms, patterns, and etches successive polymer layers of varying indices of refraction, without any drawbacks. A number of photodefinable and transparent polymers are available on the market and, thus, such lenses can be fabricated at a fraction of the cost of the silica lenses.

A second invention of the present application is directed to enabling the measurement of optical loss, electro-optical (EO) coefficient, thermo-optical (TO) coefficient, birefringence, in addition to refractive index. Knowledge of these properties is useful for designing devices with optimal numerical aperture, mode field diameter, beam profile, coupling efficiency, and other device properties.

Figure 17:
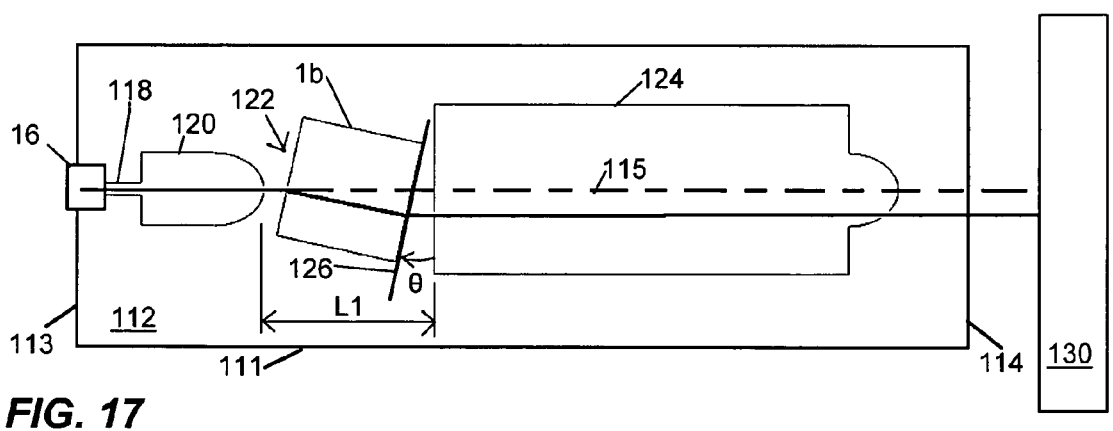
FIGS. 17-19 are top views of exemplary embodiments according to a second invention of the present application.

FIG. 17 shows a top view of a first embodiment of a second invention of the present application where the refractive index of a body of material may be measured. This embodiment is based on beam deflection due to differences in refractive index. The embodiment comprises an assembly 111 for holding a sample 1b whose refractive index is to be measured. Assembly 111 comprises substrate 112 having a top surface, a first side 113, and a second side 114. Disposed on the top surface of substrate 112 is a first planar lens 120 that has a first surface for receiving light from a waveguide 118 or other optical coupling adaptor, and a second surface opposite to the first surface. Waveguide 118 and lens 120 may have the same layer construction as waveguide 18 and lens 20 described above. The second surface of lens 120 is preferably convex. When waveguide 118 is used to couple light to lens 120 and is formed with the same layer structure as lens 120 as one continuous piece, the curvature of the first surface of lens 120 does not matter. Also disposed on the top surface of substrate 112 is a second planar lens 124 that is located opposite to first planar lens 120. Second planar lens 124 has a first surface facing the second surface of first planar lens 120 and a second surface opposite to its first surface. There is a gap 122 between the planar lenses 120 and 124 having a spacing distance L1 between the opposing surfaces of the lenses. Gap 122 is adapted to receive sample 1b, as described in greater detail below. Without sample 1b disposed in gap 122, light would propagate from first planar lens 120 to second planar lens 124 along an optical axis 115. The first surface of second planar lens 124 is preferably substantially flat and substantially perpendicular to optical axis 115. The second surface of second planar lens 124 is preferably convex. Lens 124 may have the same layer construction as lens 24 described above.

To measure the refractive index of sample 1b, it is cut to have two parallel sides (if not already formed to have such sides), and it is disposed within gap 122, with the parallel sides at an angle θ to the first surface of second planar lens 124. An alignment guide 126 may be etched or formed on substrate 112 to assist in this alignment. Angle θ may be in the range of 1-degrees to 45-degrees, and more preferably in the range of 5-degrees to 15-degrees. Sample 1b and gap 122 may be on the order of several millimeters, so conventional optical positioning techniques (e.g., combination micromanipulator and microscope) may be used to align the side of sample 1b to guide 126. A small amount removable adhesive or tacking adhesive may be used to hold sample 1b in place. Solder may also be used, as well as a thick paste, such as thermal grease. Thereafter, light is coupled to planar lens 120 and directed through sample 1b and second planar lens 124. The axis of the light is deflected as it passes through sample 1b, the amount of deflection Δd being related to the index of refraction of sample 1b and the distance between the parallel surfaces of sample 1b. If the index of refraction of sample 1b were 1.0003 (that of air), there would be no deflection. If $L_{SMP}$ is the distance between the parallel faces of sample 1d and $n_{smp}$ is the refractive index of the sample, the deflection Δd can be approximated as $$\Delta d = L_{SMP} \cdot \sin\theta \cdot \left(1 - \frac{1.0003 \cdot \cos\theta}{n_{SMP} \cdot K}\right)$$

Where K is the cosine of the internal angle within the sample, and can be estimated as:

$$K = \sqrt{1 - \left(\frac{1.0003}{n_{SMP}^*}\right)^2 \sin^2\theta},$$

where $n^*_{SMP}$ is an estimate for the index of refraction of sample 1b. The amount of deflection Δd can be measured by a beam profiler 130, which can determine the location of the maximum intensity point along one or two axes. Once the deflection Δd is measured by profiler 130 and corrected for any changes caused by second planar lens 124, the refractive index $n_{SMP}$ of the sample can be estimated by the above formulas by reverse application. Before sample 1b is placed in gap 122, beam profiler 130 may measure the location of optical axis 115 in order to calibrate the system for future measurement, or to "zero" profiler 130. Changes in the deflection caused by lens 124 can be readily determined by optical simulation of the sample in the lens structure using commercially available optical simulation software.

For a given range of index of refraction to be measured, it is well within the skill of the art to use optical simulation software to select the various dimensions and curvatures of the lenses in view of present disclosure. In addition, the change in the refractive index of sample 1b as a function of temperature, electric field, and magnetic field may be determined by using the setups shown in FIGS. 12-15, and by configuring controller 60 to control the interaction of the components, as described above in detail.

Figure 18:
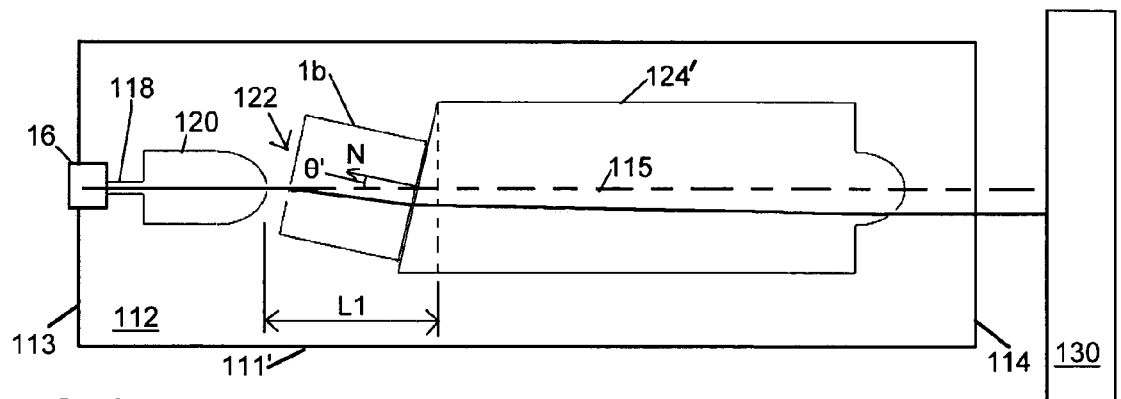

FIG. 18 shows a top view of a second embodiment 111' of the second invention of the present application where the refractive index of a body of material may be measured. This embodiment is identical to the embodiment shown in FIG. 17 except that lens 124 is replaced by lens 124', which has a first surface which is tilted with respect to optical axis 115. The normal N of the lens surface forms an angle θ' with respect to optical axis 115. Angle θ' may be in the range of 1-degree to 45-degrees, and more preferably in the range of 5-degrees to 15-degrees. Sample 1b is abutted against the tilted surface of second planar lens 124', and there is no need for the alignment guide 126 of the prior embodiment. The deflection measured by profiler 130 as a function of $n_{SMP}$ and $L_{SMP}$ is more complex to compute in mathematic form, but can be readily determined by the use of optical simulation software to construct a relationship between measured deflection and $n_{SMP}$. It is well within the ordinary skill in the art to do this in view of the teaching of the present disclosure.

For a given range of index of refraction to be measured, it is well within the skill of the art to use optical simulation software to select the various dimensions and curvatures of the lenses in view of present disclosure. In addition, the change in the refractive index of sample 1b as a function of temperature, electric field, and magnetic field may be determined by using the setups shown in FIGS. 12-15, and by configuring controller 60 to control the interaction of the components, as described above in detail.

Figure 19:
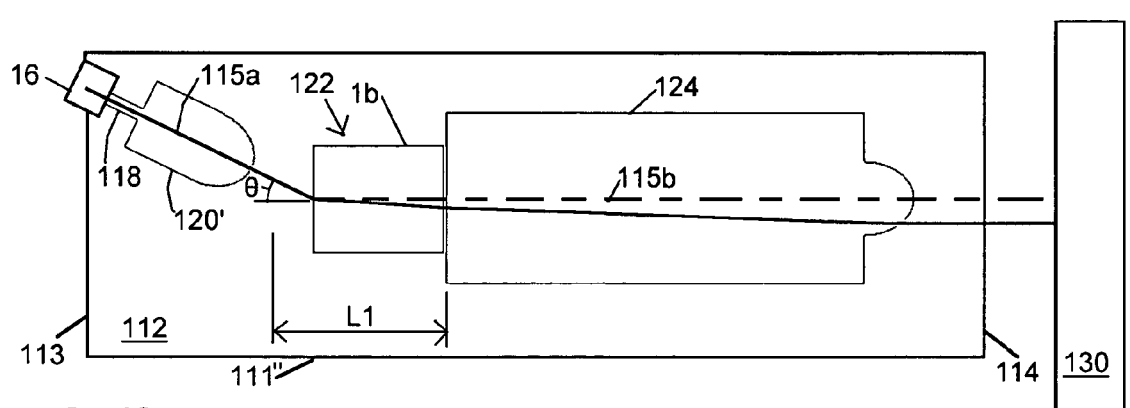

FIG. 19 shows a top view of a third embodiment 111" of the second invention of the present application where the refractive index of a body of material may be measured. This embodiment is identical to the embodiment shown in FIG. 17 except that lens 120 is replaced by lens 120', which has an optical axis 115a which is set at an angle θ" with respect to the optical axis 115b of second lens 124. Angle θ' may be in the range of 2-degrees to 45-degrees, and more preferably in the range of 5-degrees to 20-degrees. Sample 1b is abutted against the surface of second planar lens 124, and there is no need for the alignment guide 126 of the prior embodiment. The deflection measured by profiler 130 as a function of $n_{SMP}$ and $L_{SMP}$ is more complex to compute in mathematic form, but can be readily determined by the use of optical simulation software to construct a relationship between measured deflection and $n_{SMP}$. It is well within the ordinary skill in the art to do this in view of the teaching of the present disclosure.

For a given range of index of refraction to be measured, it is well within the skill of the art to use optical simulation software to select the various dimensions and curvatures of the lenses in view of present disclosure. In addition, the change in the refractive index of sample 1b as a function of temperature, electric field, and magnetic field may be determined by using the setups shown in FIGS. 12-15, and by configuring controller 60 to control the interaction of the components, as described above in detail.

Figure 20:
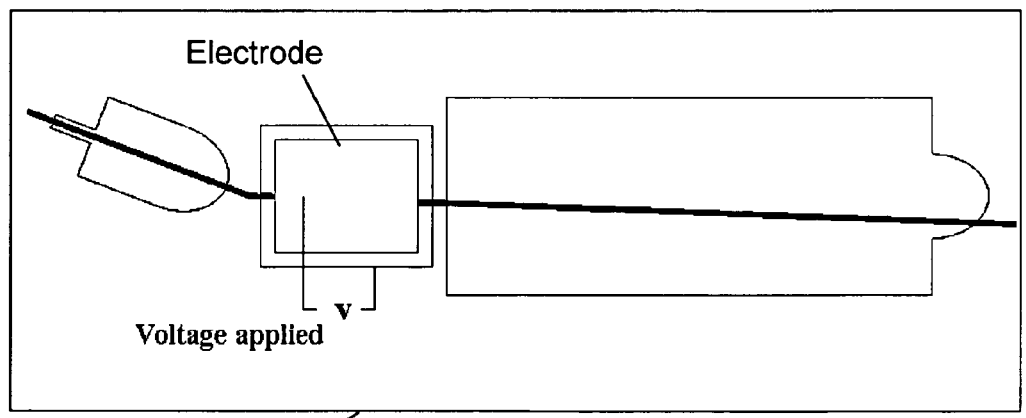
FIGS. 20-21 are top schematic views of further methods according to the second invention of the present application.
Figure 21:
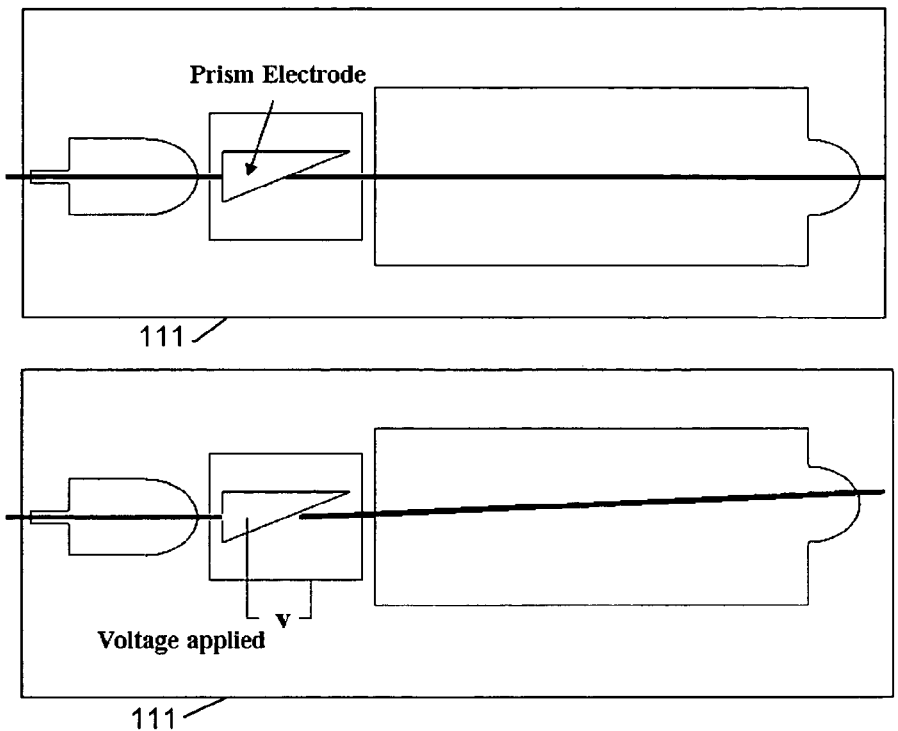

In addition, the variation of the refractive index to the electric field (specifically the electro-optic coefficient) can be measured by forming electrodes on the top and bottom surfaces of sample 1b before placing the sample in assembly 111", and thereafter applying a voltage to the electrodes while measuring the beam deflection. This is illustrated in schematic form in FIG. 20. As a modification of this approach, one or both of the electrodes may be formed in the shape of a triangle, and the sample may then be placed in assembly 111 shown in FIG. 17 with its edge parallel to the first surface of planar lens 124. This is shown schematically in FIG. 21, where the top depiction shows the case where no voltage is applied (and therefore no deflection), and where the bottom depiction shows the case where a voltage is applied. Similarly, the variation of the refractive index to temperature (specifically the thermo-optic coefficient) can be measured by elevating the sample's temperature by applying heat to the sample while measuring the beam deflection.

In all of the above embodiments, it is preferred that the area on the top surface of substrate 112, in the location between second planar lens 124 (124') and the second side 114 of the substrate be free of obstructions to the light, with the area being processed so as to be light-absorbing, or the area made as short as possible.

Figure 22:
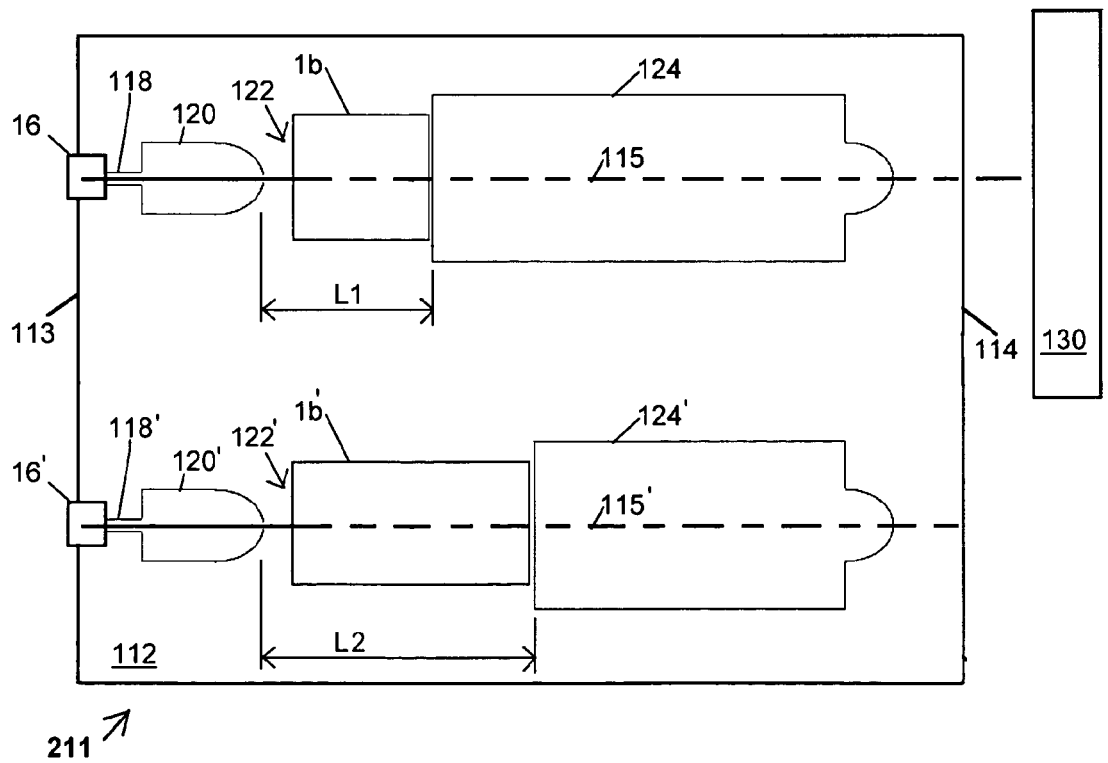
FIG. 22 is a top view of an exemplary embodiment according to a third invention of the present application.

This invention can be extended to measure another important optical property, the loss factor of the medium. This is typically difficult to measure for small samples because it is difficult to focus a test light on small samples, the losses associated with the test setup can be larger than the losses of the sample. The invention addresses these issues by using the assembly of FIG. 17 to overcome the first problem area, and by using two or more instances of the lens configuration, but with different spacing distances between lenses to allow different lengths of the sample to be measured. A difference in absorption between the two lengths can then be measured to find the loss per unit length. An exemplary assembly 211 for this is shown in FIG. 22. Two instances of assembly 111 of FIG. 17 have been integrated onto the same substrate 112, each instance using the same reference numbers as assembly 111, except that a prime symbol (') has been added to the reference numbers of the bottom instance. The two instances are identical except for the spacing distance of the gap between lenses, and the lengths of lenses 124 and 124'. The bottom instance has a larger spacing distance, which we have noted as L2 in the figure. The top instance has a smaller spacing distance, which we have noted as L1. Prior to placing the samples in the assembly, light is passed through each lens assembly, and the profiler determines the maximum intensity for each instance. These measurements will be used to normalize subsequent measurements, thereby removing the intrinsic loss in each lens assembly. As the next step, samples 1b and 1b' of the same material, but of different lengths, are placed into respective gaps 122 and 122'. Light is directed through each sample, and the profiler determines the maximum intensity for each instance, with the samples present. These measured intensities are divided by the respective measurements made without samples present to normalize them. The normalized values are then divided to find the loss for the difference in length between the two samples.

In addition to characterizing loss properties, the above assemblies can be used to quantify birefringence effects using a similar methodology.

Since the above embodiments are substrate-based, they may be manufactured with conventional semiconductor processing steps, and made with high precision and low cost compared to conventional optics approaches that use micro-manipulator stages to hold and align components. In addition, misalignment of the components is minimized. Moreover, each assembly can be reused.

Figure 23:
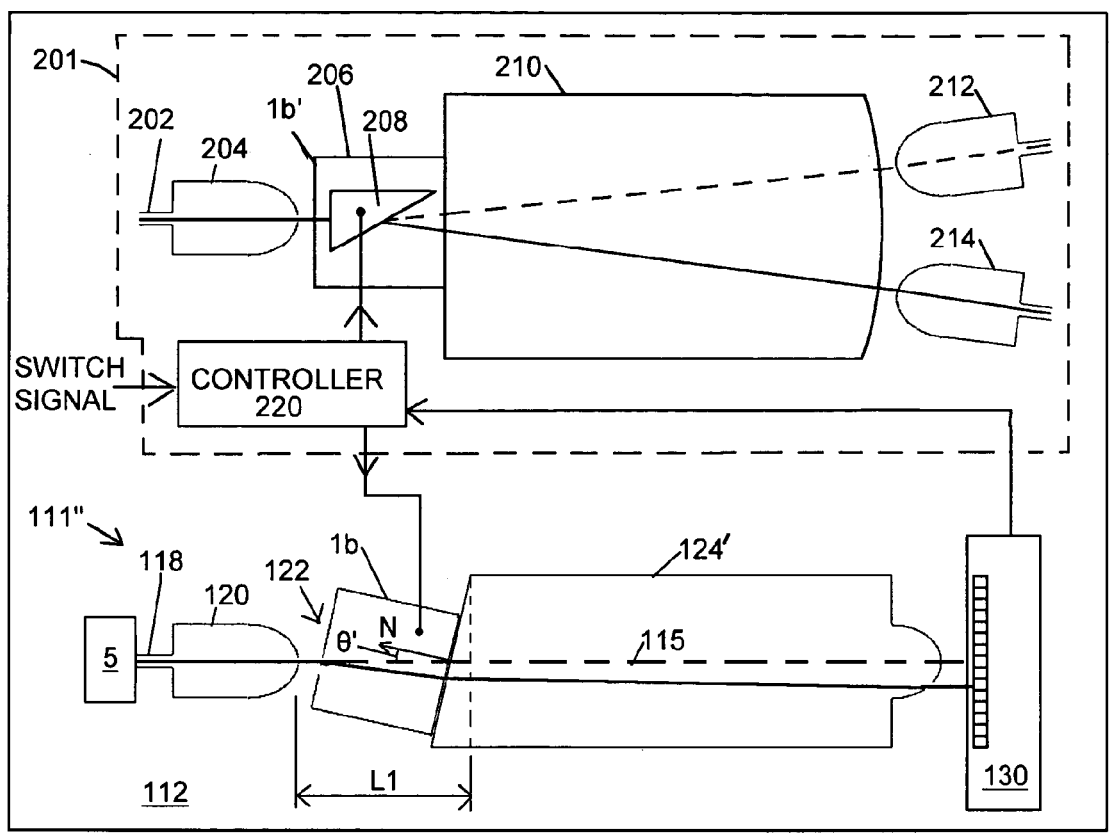
FIG. 23 is a top view of an exemplary embodiment according to a fourth invention of the present application.

As a fourth invention of the present application, a lens structure is integrated on a substrate in close proximity to an optical device to monitor the properties of an optical material of the device during operation, such as over long periods of time. The lens structure has a gap between two lenses, with the gap being filled with the optical material of the device to be monitored. The lens structure can be from any of assemblies 11, 111, 111', and 111" (FIG. 6, FIGS. 17-19). An embodiment of the fourth invention is shown at 200 in FIG. 23, where assembly 111' (FIG. 18) and light source 5 have been integrated on substrate 112 with an optical device 201, which may take any form and may be used for any purpose. The exemplary optical device 201 comprises a 1×2 optical switch having an input waveguide 202 that conveys light to a collimating lens 204. The collimated light is provided as an input to an optic deflector 206, which comprises a body of electro-optic material 1b' and a triangular shaped electrode 208. Deflector 206 is commonly known as a prism deflector, and the electrode is commonly known as a prism electrode. A voltage applied to electrode 208 causes the refractive index of material 1b' to change with respect to the material that is not covered by electrode 208. This causes a difference in refractive index, which in turn causes the beam to deflect in relation to the applied voltage because the triangle cuts across the beam's axis. A ground electrode may be formed below the body of material 1b', or the substrate 112 may be used as a ground electrode.

A positive voltage deflects the beam in one direction, while a negative voltage deflects the beam in the opposite direction. Two directions thus arise, allowing the input signal to be diverted to one of two outputs to provide the 1×2 switch. Deflector 206 is abutted against a slab waveguide 210 to couple its output thereto. Slab waveguide 210 enables the two possible deflected beam paths to develop some spatial separation so they may be collected by respective focusing lenses 212 and 214. The focusing lenses feed respective output waveguides. Slab waveguide 210 has a curved exit surface to assist in focusing.

A controller 220 receives an input switch signal which indicates the desired optical coupling of the input signal to one of the two output signals. Conventionally, controller 220 would be initially calibrated to apply the required voltages to effect the couplings. These voltages would remain in place until the end-of-use of the device. A problem arises, however, in that the optical properties of material 1b change with time, which can cause degradation in the optical coupling of the signal to the outputs. In the fourth invention, a representative sample 1b of the electro-optic material is monitored by an embodiment of assembly 111", light source 5, and beam deflection profiler 130. Beam profiler 130 may comprise an array of closely spaced photo-detectors to sense the position of the deflected beam, and circuitry that provides controller 220 with an indication of the deflection or an indication of the refractive index. Using this information, controller 220 may comprise a pre-stored relationship (such as in the form of a table or mathematical equation) of the applied voltages to use for deflector 206 based on the measured results provided by source 3, assembly 111", and profiler 130. The relationship may indicate the absolute voltage values to use, or may indicate delta voltage corrections from base voltage values. As a further feature, an electrode may be formed on the top surface of sample 1b, and the controller may apply various voltages to sample 1b as part of the monitoring process.

In the above way, the controller is able to modify its control signals to the optical device in order to compensate for changes in the properties of the device's electro-optic material due to temperature, humidity, electric fields, magnetic fields, aging, etc.

It may be appreciated that the fourth embodiment may also be practiced using apparatus 10 shown in FIG. 6. In this case, the electro-optic material 1b' for the optical device and for substance 1 may be formed from a liquid and subsequently cured to a solid state. The beam profiler 30 may also comprise an array of photo-detectors and internal analog circuitry and digital circuitry that determines the beam width from the relative intensities on the photo-detectors. For this, the input of a single analog-to-digital conversion circuit may be multiplexed between the outputs of the photo-detectors to find the relative spatial intensity of the beam, and the digital circuitry may compare the detector outputs against the center detector's output to estimate the beam width.

While the present invention has been particularly described with respect to the illustrated embodiments, it will be appreciated that various alterations, modifications and adaptations may be made based on the present disclosure, and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the appended claims.

What is claimed is:

1. An apparatus for measuring the refractive index of a substance, said apparatus comprising:
   a first lens;
   a second lens disposed opposite to the first lens along an optical axis;
   a gap between the first and second lenses, the gap adapted to receive the substance;
   a beam profiler disposed to receive light passed from the first lens through the gap and the second lens, and to measure a beam width of the received light; and a controller that estimates the refractive index of the substance from a measured beam width and a relationship between refractive index and beam width.

2. The apparatus of claim 1, wherein light exiting the second lens has a converging section and a diverging section, the converging section being closer to the second lens than the diverging section, and wherein the beam profiler has an optical capture window that is positioned in the diverging section.

3. The apparatus of claim 1 further comprising a substrate, and
wherein the first lens comprises a planar spreading lens disposed on the substrate, the planar spreading lens having a first surface for receiving light and a second surface opposite to the first surface; and
wherein the second lens comprises a planar converging lens disposed on the substrate, the planar converging Lens having a first surface facing the second surface of the planar spreading lens and a second surface opposite to the first surface.

4. The apparatus of claim 3 further comprising a waveguide disposed on the substrate to couple light to the first surface of the planar spreading lens.

5. The apparatus of claim 3 further comprising a recess formed in the substrate, a first portion of the recess being disposed adjacent to the gap and a second portion being disposed under at least a portion of the gap.

6. The apparatus of claim 3 further comprising a fixture having a first retainer for holding the substrate and a second retainer for attaching to an optical capture element of the beam profiler.

7. The apparatus of claim 3 wherein the optical axis passes through the planar spreading lens and the planar converging lens, wherein the second surface of the planar spreading lens has a curvature that follows the contour of an ellipse, the ellipse having a first axis ($P_s$) that is parallel to the optical axis and a second axis ($T_s$) that is transverse to the optical axis.

8. The apparatus of claim 7 wherein the first axis is longer than the second axis.

9. The apparatus of claim 3 wherein the optical axis passes through the planar spreading tens and the planar converging lens, wherein the first surface of the planar converging lens has a curvature that follows the contour of an ellipse, the ellipse having a first axis ($P_c$) that is parallel to the optical axis and a second axis ($T_c$) that is transverse to the optical axis.

10. The apparatus of claim 9 wherein the first axis is longer than the second axis.

11. The apparatus of claim 3 further comprising a heater element disposed on at least one of the planar lenses, and a temperature sensor.

12. The apparatus of claim 3 further comprising a heater element disposed in the gap, and a temperature sensor.

13. The apparatus of claim 3 further comprising a first electrode and a second electrode positioned to generate an electric field that passes through at least the gap.

14. The apparatus of claim 3 further comprising a coil that generates a magnetic field that passes through at least the gap.

15. The apparatus of claim 1 further comprising a first capillary guide disposed at an edge of the first lens, and a second capillary guide disposed at an edge of the second lens, the first and second capillary guides providing an opening for the substance which is wider than a distance between the first and second lenses.

16. The apparatus of claim 1 further comprising a source of heat and a temperature sensor.

17. A method for measuring the refractive index of a substance, comprising the steps of:
(a) disposing the substance between a first lens and a second lens;
(b) passing light from the first lens to the second lens through the substance;
(c) measuring the beam width of the light exiting the second lens; and
(d) outputting a signal representative of an estimated value for the refractive index of the substance, the estimated value being generated from the measured beam width and a relationship between refractive index and beam width.

18. The method of claim 17 wherein the substance is in liquid form.

19. The method of claim 17 wherein step (a) comprises the steps of disposing the substance in liquid form between the lenses, and thereafter converting the substance to a solid form.

20. The method of claim 17 further comprising the step of heating the substance during steps (b) and (c) to one or more temperatures above room temperature.

21. The method of claim 17 further comprising the step of cooling the substance during steps (b) and (c).

22. The method of claim 17 further comprising the step of applying an electric field to the substance during steps (b) and (c).

23. The method of claim 17 further comprising the step of applying a magnetic field to the substance during steps (b) and (c).

24. The method of claim 17 further comprising the step of varying the wavelength of the light during steps (b) and (c).

25. The method of claim 17 wherein the first lens comprises a planar spreading lens formed on a substrate, and wherein the second lens comprises a planar converging lens formed on said substrate.

26. The method of claim 17, wherein the light exiting the second lens has a converging section and a diverging section, the converging section being closer to the second lens than the diverging section, and wherein step (c) comprises measuring the beam width of the exiting light in the diverging section.

* * * * *

UNITED STATES PATENT AND TRADEMARK OFFICE
CERTIFICATE OF CORRECTION

PATENT NO. : 7,283,220 B2
APPLICATION NO. : 10/808665
DATED : October 16, 2007
INVENTOR(S) : Lidu Huang et al.

It is certified that error appears in the above-identified patent and that said Letters Patent is hereby corrected as shown below:

Col. 1, Ln. 23: After "an" delete "1 MF" and insert --IMF--;

Col. 7, Ln. 65: After "using." delete "BeamScan profiler®" and insert --BeamScan® profiler--;

Col. 19, Ln. 42: After "spreading" delete "tens" and insert --lens--.

Signed and Sealed this

Twenty-ninth Day of December, 2009

David J. Kappos
*Director of the United States Patent and Trademark Office*